United States Patent [19]
Casagrande et al.

[11] Patent Number: 5,571,834
[45] Date of Patent: Nov. 5, 1996

[54] PHARMACEUTICAL COMPOSITION USEFUL FOR THE TREATMENT OF CARDIOVASCULAR DISEASES

[75] Inventors: Cesare Casagrande, Arese; Luciano Licciardello, Monza, both of Italy

[73] Assignee: Zambon Group S.p.A., Vicenza, Italy

[21] Appl. No.: 186,177

[22] Filed: Jan. 25, 1994

Related U.S. Application Data

[63] Continuation of Ser. No. 378,036, Jul. 11, 1989, Pat. No. 5,304,570.

[30] Foreign Application Priority Data

Jul. 15, 1988 [IT] Italy ................................. 21369A/88

[51] Int. Cl.⁶ ..................... A61K 31/40; A61K 31/225
[52] U.S. Cl. ............................. 514/423; 514/548
[58] Field of Search ........................ 514/423, 548

[56] References Cited

U.S. PATENT DOCUMENTS

| | | | |
|---|---|---|---|
| 4,218,470 | 3/1984 | Simes | 514/548 |
| 4,302,471 | 4/1981 | Casagrande | 514/548 |
| 4,677,102 | 6/1987 | Baldwin et al. | 514/218 |
| 4,698,356 | 10/1987 | Ryan et al. | 548/531 |
| 4,983,598 | 1/1991 | Cavero et al. | 514/423 |

FOREIGN PATENT DOCUMENTS 2845499  5/1979  Germany.

OTHER PUBLICATIONS

Cantelli, *Cardiovascular Drugs and Therapy*, vol. 2, pp. 83 to 91 1988.
Packer, JACC, pp. 171–173, 1985.
Cleland, J. Cardiovascular Pharmacol., 8, pp. 700–706, 1986.
Saki, Arch. Int. Med., 149, pp. 669–673, 1989.
Packer, J. Cardiovascular Pharmacol., 10:Suppl. 7, pp. 583–587, 1987.
Packer, N. Engl. J. Med., 315, pp. 847–853, 1986.
Ghiringhelli, Current Therapeutic Research, 48, No. 1, pp. 96–111, 1990.
(Terrachini), reprinted from *Current Therapeutic Research*, vol. 5 No. 6, pp. 753 to 761, 1991.

*Primary Examiner*—Jerome D. Goldberg
*Attorney, Agent, or Firm*—Jacobson, Price, Holman & Stern, PLLC

[57] ABSTRACT

A pharmaceutical composition is described comprising ibopamine and an ACE-inhibitor.

Such composition is useful in the treatment of cardiovascular diseases, more particularly of hypertension and heart insufficiency even when the latter is associated with or caused by hypertension.

15 Claims, No Drawings

PHARMACEUTICAL COMPOSITION USEFUL FOR THE TREATMENT OF CARDIOVASCULAR DISEASES

This is a continuation of application Ser. No. 07/378,036, filed Jul. 11, 1989, now U.S. Pat. No. 5,304,570.

This invention relates to a composition comprising ibopamine and an ACE-inhibitor.

Ibopamine (diisobutyril ester of epinine) is a drug useful in cardiovascular therapy and has been described in U.S. Pat. Nos. 4,218,470 and 4,302,471. Ibopamine has a complex pharmacological effect based on the stimulation of dopaminergic, alpha-adrenergic and beta-adrenergic receptors. In particular, ibopamine does not modify the blood pressure and the heart rate either in normal subjects or in patients suffering from heart and renal insufficiency, but it shows advantageous effects in heart insufficiency therapy due to its ability of increasing heart delivery and blood flow towards organs and muscles, thus improving perfusion of vital organs, such as the heart, kidney, brain, and skeletal muscles.

Ibopamine may be administered helpfully over a long period by mouth.

While (in the therapy of heart insufficiency associated with or caused by hypertension) ibopamine was not used due to potential effects on alpha-adrenergic receptors and possible hypertensive effects, it has recently been discovered that ibopamine is capable of inducing a moderate and gradual drop in blood pressure in hypertensive patients without affecting blood pressure when the latter is normal, both in healthy subjects and in cardiovascular and renal pathologies, as mentioned above, and indeed it can help in restoring blood pressure in patients suffering from renal insufficiency which are subjected to dialysis with consequent hypovolemia and drop in blood pressure.

ACE-inhibitors, that is, the Angiotensin Converting Enzyme inhibitors, are widely used as antihypertensive drugs.

In some patients, however, ACE-inhibitors cause drops in blood pressure and impairment of the renal function with an increase of azotemia and of plasma creatinine. Specific examples of ACE-inhibitors are:

captopril (Merck Index, 10th Edition, No. 1747, page 244)

enalapril (Merck Index, 10th Edition, no. A-5, APP. 1)

ramipril (HOE-498) (Annual Drug Data Report 6, 137 (1984))

quinepril (Annual Drug Data Report 5, 41 (1983))

trandolapril (Annual Drug Data Report 7, 768 (1985))

zofenopril (Annual Drug Data Report 6, 162 (1984))

pivopril (Annual Drug Data Report 8, 146 (1986))

cilazaprilat (Annual Drug Data Report 8, 32 (1986))

phenacein (Annual Drug Data Report 7, 20 (1985))

perindopril (S-9490) (Annual Drug Data Report 7, 99 (1985))

pentopril (CGS-13945) (Annual Drug Data Report 5, 40 (1983))

delapril (CV-3317) (Annual Drug Data Report 6, 12 (1984))

cilazapril (Annual Drug Data Report 7, 579 (1985))

ancovenin (Annual Drug Data Report 6, 20 (1984))

lisinopril (MK-521) (Annual Drug Data Report 5, 124 (1983))

alacepril (Japanese Patent Application No. 78/82809)

fosenopril (U.S. Patent No. 4,656,188)

nicotianamin (East Germany Patent DD 226 880).

Now, it has been unexpectedly found that the combined administration of ibopamine together with an ACE-inhibitor is helpful in the therapy of cardiovascular diseases, as ibopamine overcomes the drawbacks and the side effects of ACE-inhibitors not only in heart insufficiency, but also in hypertension therapy, where ACE-inhibitors are widely used, whereas ibopamine was not used previously.

It has also been found that the blood pressure drop induced by ibopamine in hypertensive patients may be further enhanced, with no drawbacks and with no side effects, by the combined use of ibopamine and an ACE-inhibitor.

Therefore, it is one object of the present invention to provide a pharmaceutical composition which is useful in the therapy of cardiovascular diseases and comprises ibopamine and an ACE-inhibitor.

In particular, said pharmaceutical composition is useful in the treatment of hypertension, heart insufficiency and heart insufficiency associated with hypertension, as the combination of ibopamine with an ACE-inhibitor reduces or removes the negative effects of ACE-inhibitors. Said composition is therefore a particularly suitable and innovative means for the treatment of heart insufficiency having different etiology (dilatative, ischemic, alcoholic) even when the latter is associated with hypertension, as well as for the treatment of the hypertension etiology.

The advantages of the combined therapy have been revealed by an improvement of the heart functionality with low or moderate doses of ACE-inhibitors; marked increases in heart delivery have been observed and, in prolonged treatment, also symptomatic and functional improvements of patients without a drop in pressure below the values compatible with their circulatory conditions, in particular as regards the systolic pressure. This has proved particularly advantageous in older patients with limited renal functionality and limited heart and brain irrigation. In particular, in addition to the lack of pressure drops, deterioration of the renal function with increase of azotemia and of the level of plasma creatinine have proved absent.

In a certain number of patients the side effects of this type limit the therapeutic use of ACE-inhibitors, or allow their administration only at reduced doses, which are not in themselves adequately effective.

The reasons for the unexpected beneficial effects of the combined therapy are not known since the complexity of the pharmacological effects of ibopamine and the complexity of the feed-back mechanism operating after ACE inhibition do not allow the advance of conclusive hypotheses.

However, the ability of ibopamine of improving perfusion of organs with a dual effect on heart stimulation and vasodilatation allows a better balancing of pressure adjustment to the metabolic requirements of the organs and to the emunctory function of the kidney.

The effects mediated by the $DA_2$-dopaminergic receptors on the sympathorenal interactions (reduction of the sympathetic tone and reduction of the secretion of aldosterone and renine) are probably at the origin of the lack of deterioration of the renal function and of the preservation of the glomeruli filtration.

For the therapeutical purpose ibopamine or a pharmaceutically acceptable acid addition salt thereof and an ACE-inhibitor are preferably incorporated in a pharmaceutical dosage form suitable for oral, rectal, parenteral or topical administration.

Depending on the desired administration route, the compositions of this invention will be in the form of tablets, capsules, dragees, syrup, drops and the like for oral administration; of suppositories for rectal administration; of solution, suspensions and emulsions ready for parenteral administration or which are extemporaneously prepared by diluting a lyophilized preparation; of ointments, creams or medicated adhesive bendages for topical administration.

Furthermore, for oral administration, slow-release compositions may also be used.

Preferred dosage forms according to this invention are the solid forms for oral administration.

Besides ibopamine or a pharmaceutically-acceptable acid addition salt thereof, such as hydrochloride, and an ACE-inhibitor or a pharmaceutically-acceptable salt thereof, the compositions of this invention comprise a carrier or an inert diluent (either solid or liquid) and, optionally, other additives suitable for pharmaceutical use, and are prepared according to usual techniques.

The effective dose of ibopamine and of an ACE-inhibitor in the composition of this invention will vary depending on various factors, such as the individual response, the age, and the general condition of the patient, as well as the intended administration route.

In general, however, the composition of this invention will contain from 50 to 100 mg of ibopamine, or the equivalent amount of a pharmaceutically acceptable acid addition salt thereof, and from the standard dose to ⅕ of said standard dose of an ACE-inhibitor or the equivalent amount of a pharmaceutically-acceptable salt or of a pro-drug thereof. As used herein the expression "standard dose" means the known usual dose of said ACE-inhibitor.

Typical examples of preferred ACE-inhibitors according to this invention are captopril, alacepril, enalapril, lisinapril, cilazapril and ramapril.

In general the ACE-inhibitor according to this invention will be preferably selected from those which are currently administered 2–3 times a day in the same manner as ibopamine.

A preferred embodiment of this invention contemplates replacement of the ACE-inhibitor drug with a suitable pro-drug thereof.

For example, it has been found that captopril may be helpfully replaced by equimolecular amounts of the S-benzoyl-derivative (described in European Patent No. 0 008 831) or of the S-(methoxybenzoyl)-derivative thereof.

The latter, that is (S,S)-N-(3-(4-methoxybenzoyl-thio)-2-methyl-propionyl)-proline, is novel and is a further object of the present invention.

Its preparation, described in detail in Example 5, is performed by reacting captopril, (S,S)-N-(3-mercapto-2-methyl- propionyl)-proline, with 4-methoxybenzoyl chloride in the presence of a base.

A still further object of this invention is to provide a method for treating cardiovascular diseases comprising administering to a subject suffering from hypertension, heart insufficiency or heart insufficiency associated with hypertension a composition containing ibopamine or a pharmaceutically acceptable salt thereof and an ACE-inhibitor or a pharmaceutically acceptable salt or a pro-drug thereof. In order to better illustrate the present invention without however limiting it, the following examples are now given.

EXAMPLE 1

Tablets

| | |
|---|---|
| Ibopamine hydrochloride | 112 mg |
| (S,S)-N-(3-mercapto-2-methyl-propionyl)-proline (captopril) | 12.5 mg |
| Microcrystalline cellulose | 46.5 mg |
| Polyvinyl-2-pyrrolidone | 3 mg |
| Crospovidone | 6 mg |
| Hydrogenated castor oil | 2 mg |
| | 182.0 mg |

The active ingredients are weighed accurately and sieved.

They are then mixed together and with a part of the microcrystalline cellulose.

The mixture is granulated with a solution of polyvinyl-2-pyrrolidone, sieved and dried for one night. The remaining cellulose is then added to the granulate together with crospovidone and hydrogenated castor oil, sieved and then mixed for a few minutes. Finally, the so obtained granulate is compressed according to usual techniques.

Working in a similar manner tablets have been prepared containing, instead of captopril, equimolecolar amounts of enalapril and ramipril, respectively.

EXAMPLE 2

Working as in Example 1, tablets are prepared with the following composition:

| | |
|---|---|
| Ibopamine hydrochloride | 112 mg |
| (S,S)-N-(3-mercapto-2-methyl-propionyl)-proline (captopril) | 25 mg |
| Microcrystalline cellulose | 50 mg |
| Polyvinyl-2-pyrrolidone | 4 mg |
| Crospovidone | 6 mg |
| Hydrogenated castor oil | 3 mg |
| | 200 mg |

EXAMPLE 3

Film-coated Tablets

| A-Tablet Composition: | |
|---|---|
| Ibopamine hydrochloride | 112 mg |
| (S,S)-N-(3-(4-methoxybenzoylthio)-2-methyl-propionyl)-proline | 20 mg |
| Microcrystalline cellulose | 50 mg |
| Polyvinyl-2-pyrrolidone | 4 mg |
| Crospovidone | 6 mg |
| Hydrogenated castor oil | 3 mg |
| | 195 mg |
| B-Coating Composition: | |
| Hydroxy propyl methyl cellulose | 3.3 mg |
| Polyethylene glycol 6000 | 0.7 mg |
| Titanium dioxide | 2 mg |
| | 201.0 mg |

The tablets are prepared with a process similar to that of Example 1 and subsequently coated in a basin with an insulating coating followed by an opaque coating based on titanium dioxide. Coating occurs with an aqueous solution of hydroxy propyl methyl cellulose and polyethylene glycol in the proportions indicated above, followed by a second portion of the same solution, in which the titanium oxide is suspended, according to the usual film-coating technique.

Working in a similar manner film-coated tablets have been prepared which, in place of the S-(4-methoxy-benzoyl) derivative of captopril, contain an equimolecular amount of the S-benzoyl derivative.

EXAMPLE 4

A group of 6 patients suffering from essential hypertension of a moderate degree on a diet with a controlled amount of sodium (100 mEq die) has been treated for 5 days with ibopamine at a dose of 100 mg three times a day and then for a further 5 days with three tablets of Example 2 a day.

The following values of blood pressure (AP) and heart beat (*=p<0.05) have been measured

|  | Syst. AP (mmHg) | Diastol. AP (mmHg) | FC (beats/min) |
|---|---|---|---|
| Initial | 159 ± 5.9 | 98 ± 3.4* | 75 |
| 5th day | 150 ± 5.8* | 94 ± 2.1* | 77 |
| 10th day | 147 ± 4.7 | 88 ± 2.4* | 75 |

EXAMPLE 5

Preparation of (S,S)-N-(3-(4-methoxybenzoyl-thio)-2-methylpropionyl)-proline.

To a solution of (S,S)-N-(3-mercapto-2-methyl-propionyl)-proline (20 g; 0.02 mol) in 0.5 N NaOH (184 ml; 0.092 mol) are added simultaneously, while keeping the pH at about 9 and temperature at from 0° to 5° C., a solution of 40% (w/v) NaOH (13.8 ml; 0.138 mol) and 4-methoxybenzoyl chloride (18.8 g; 0.11 mol).

When the addition is over, the said temperature is maintained for 30 minutes. The reaction mixture is then made acid with concentrate HCl. After a further 30 minutes under stirring, the solid product is collected by filtration and crystallized from ethyl acetate. 27 g (Yield, 84%) of (S,S)-N-(3-(4-methoxybenzoyl-thio)-2-methyl-propionyl)-proline are thus obtained, m.p. 140°–141° C.

We claim:

1. A pharmaceutical composition useful for treating cardiovascular disease and comprising a pharmaceutically-acceptable carrier and an effective enhanced amount combination of a) ibopamine or a pharmaceutically-acceptable salt thereof and b) an enalapril or pharmaceutically-acceptable salt thereof.

2. A composition according to claim 1 wherein component (a) is the hydrochloride salt of ibopamine.

3. A composition according to claim 1 wherein the amount of (a) is sufficient to overcome drawbacks or side effects of (b).

4. A pharmaceutical composition of claim 1 wherein the amount of component (b) is sufficient to enhance a blood pressure drop induced by component (a) in hypertensive patients.

5. A composition according to claim 1 wherein the amount of component (b) is from 0.2 to the standard dose of that component for each 50 to 100 mg of ibopamine or the equivalent amount of a pharmaceutically-acceptable acid-addition salt thereof.

6. A method for treating cardiovascular disease comprising administering an effective amount of a composition according to claim 1 to a subject suffering from hypertension, heart insufficiency or heart insufficiency associated with hypertension.

7. In cardiovascular therapy which comprises administering enalapril or a pharmaceutically-acceptable salt thereof to a patient in need of such therapy, the improvement which comprises at least substantially concurrently administering an enhancing effective amount of ibopamine or a pharmaceutically-acceptable salt thereof to the patient.

8. The therapy of claim 7 for treating a patient afflicted with hypertension.

9. The therapy of claim 7 for treating a patient afflicted with heart insufficiency.

10. The theray of claim 7 wherein enalapril or a pharmaceutically-acceptable salt thereof is administered in an amount within a range of from a standard dose thereof to ⅕ of said standard dose.

11. The therapy of claim 7 wherein the effective amount ibopamine or a pharmaceutically-acceptable salt thereof is within the range of from 50 to 100 mg.

12. A method of reducing side effects in cardiovascular therapy with enalapril or a pharmaceutically-acceptable salt thereof which comprises jointly administering an effective amount of ibopamine or a pharmaceutically-acceptable salt thereof to a patient undergoing such therapy.

13. A method of claim 12 of counteracting an increase of azotemia or of plasma creatinine in treating cardiovascular disease in a patient to whom enalapril or a pharmaceutically-acceptable salt thereof is administered, which method comprises concurrent administration of an effective amount of ibopamine or a pharmaceutically-acceptable salt thereof.

14. A method of claim 12 wherein the patient is afflicted with hypertension.

15. A method of claim 12 wherein the patient is afflicted with heart insufficiency.

* * * * *